United States Patent [19]

Langer et al.

[11] Patent Number: 5,292,953

[45] Date of Patent: Mar. 8, 1994

[54] PROCESS FOR THE PREPARATION OF AZOMETHINES

[75] Inventors: Reinhard Langer; Hans-Josef Buysch, both of Krefeld; Paul Wagner, Duesseldorf, all of Fed. Rep. of Germany

[73] Assignee: Bayer Aktiengesellschaft, Leverkusen, Fed. Rep. of Germany

[21] Appl. No.: 57,199

[22] Filed: May 3, 1993

Related U.S. Application Data

[63] Continuation of Ser. No. 739,116, Jul. 31, 1991, abandoned.

[30] Foreign Application Priority Data

Aug. 9, 1990 [DE] Fed. Rep. of Germany ....... 4025185

[51] Int. Cl.$^5$ ............................................ C07C 249/02
[52] U.S. Cl. .................................... 564/277; 564/271; 564/276
[58] Field of Search ................. 564/277, 271, 276

[56] References Cited

U.S. PATENT DOCUMENTS

| | | | |
|---|---|---|---|
| 2,336,215 | 12/1943 | Bean | 564/276 |
| 4,045,486 | 8/1977 | Krall et al. | 260/566 R |
| 4,281,195 | 7/1981 | George | 564/271 |

FOREIGN PATENT DOCUMENTS

| | | |
|---|---|---|
| 1078119 | 9/1960 | Fed. Rep. of Germany . |
| 1134076 | 8/1962 | Fed. Rep. of Germany . |
| 2244169 | 3/1973 | Fed. Rep. of Germany . |
| 2244238 | 3/1973 | Fed. Rep. of Germany . |
| 2525295 | 12/1976 | Fed. Rep. of Germany . |
| 2901863 | 7/1980 | Fed. Rep. of Germany . |

Primary Examiner—Allen J. Robinson
Assistant Examiner—Peter O'Sullivan
Attorney, Agent, or Firm—Sprung Horn Kramer & Woods

[57] ABSTRACT

Azomethines can be prepared by the condensation of cycloalkanones and anilines in the presence of acid heterogeneous catalysts, with azeotropic removal of the water of reaction, the condensation being carried out in a continuous reaction in a column-like reactor having an applied temperature profile, and the starting materials being fed in the low-temperature zone and, of the reaction products, the water of reaction to be removed as an azeotrope also being removed in the low-temperature zone and the azomethine formed being removed in the high-temperature zone.

19 Claims, No Drawings

PROCESS FOR THE PREPARATION OF AZOMETHINES

This application is a continuation, of application Ser. No. 739,116 filed Jul. 31, 1991, now abandoned.

BACKGROUND OF THE INVENTION

1. Field of the Invention

The present invention relates to a process for the condensation of optionally substituted cycloalkanones with optionally substituted anilines with the formation of azomethines in a continuous reaction in a column-like reactor having an applied temperature profile.

2. Description of the Related Art

The condensation of cyclohexanone and aniline to give cyclohexylideneaniline using zinc chloride as catalyst has been known for a long time (Ber. 53 (1920), 345-354). The catalyst system $HCl-ZnCl_2$ has been employed in such condensation reactions for difficult cases (Ber. 46 (1913), 2718).

The condensation of aromatic amines with cyclohexanones is an equilibrium reaction with a slight heat change. It is shifted in favour of the azomethine (Schiff's base) if the water formed in the reaction is removed from the system. In general, this is achieved by means of azeotropic distillation, if appropriate, employing an inert entraining agent, such as benzene, toluene and the like, for this purpose. Recently the use of $TiCl_4$ (J. Org. Chem. 32 (1967), 3247) or of molar amounts of $(butyl)_2SnCl_2$ (Synth. Commun. 12 (1982), 495) has been described for fixing the water of reaction. Both compounds fix the water formed in the reaction with the liberation of HCl.

Other developments have been aimed at fixing the water-fixing species to the aniline by means of a covalent bond, for example in the form of N,N-bis-(trimethylsilyl)-aniline (Bull. Soc. Chim. Fr. 1966, 3205), iminophosphoranes (Angew. Chem. Int. Ed. Eng. 5 (1966), 947) and N-(diphenylaluminium)-aniline (J. Org. Chem. 51 (1986), 1848).

Another method of fixing the water formed in the reaction effectively and thus enabling the reaction to be carried out under mild conditions with a low excess of aniline or ketone, is the use of molecular sieves (J. Org. Chem. 36 (1971), 1570; German Offenlegungsschrift 2,244,238). The disadvantage of this last-mentioned process is the involved and expensive regeneration of the molecular sieve.

Azeotropic removal of water is thus certainly the process of the greatest industrial interest, if it is possible to obtain acceptable reaction times using a small excess of one of the two components, without having to employ major amounts of azeotropic entraining agent.

The condensation of N-phenyl-p-phenylenediamine with cyclohexanone without the addition of a catalyst is described in German Auslegeschrift 1,078,119; in this case it is necessary to employ an excess of cyclohexanone of 200 to 300%.

It is shown in German Offenlegungsschrift 2,525,295 that the reaction time in the condensation of aniline with a 400% excess of cyclohexanone in the absence of a catalyst increases greatly as the batch size increases, so that scaling up to an industrial scale is not possible. It has also been shown that strongly acid and weakly acid organic resins have a favourable effect on the reaction time.

In German Offenlegungsschrift 2,901,863 freshly synthesised, anhydrous, non-calcined calcium hydrogenphophate, apatite of the formula $Ca_5(PO_4)_3OH$, dried, noncalcined aluminium oxide-hydroxides and proton-exchanged, aluminium silicates of the montmorillonite type which have been washed until neutral are described as effective catalysts for the reaction of aromatic amines with ketones. The examples in this patent application are limited, however, to the condensation of p-phenylenediamine, which is reactive, with methyl isobutyl ketone, a 150% excess of ketone being used.

SUMMARY OF THE INVENTION

It was thus desirable to develop a low-cost process which does not pollute the environment for the synthesis of cycloalkylideneanilines, which is distinguished by high yields, simple apparatus and optimum utilisation of energy with a minimum input of energy.

A process has been found by means of which the azomethine compound can be obtained in a high yield and in a high state of purity using a minimum excess of carbonyl or aniline component and in a continuous process.

A process has been found for the preparation of azomethines of the formula

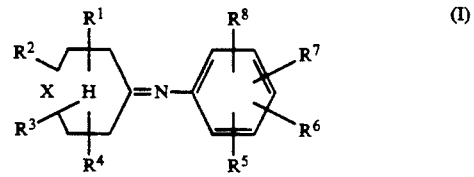

in which $R^1$, $R^2$, $R^3$, $R^4$, $R^5$, $R^6$, $R^7$ and $R^8$ independently of one another denote hydrogen, linear or branched $C_1-C_6$-alkyl, $C_3-C_6$-cycloalkyl or aryl, and $R^5$, $R^6$, $R^7$ and $R^8$ independently of one another additionally denote halogen, linear or branched $C_1-C_6$-alkoxy, hydroxyl, amino, $C_1-C_6$-alkylamino, di-$C_1-C_6$-alkylamino, aryloxy or arylamino, aryl representing phenyl or 5-membered or 6-membered heteroaryl attached in the 2-, 3- or 4-position and having 1 or 2 hetero atoms belonging to the group N, O and S, and X denotes $-CH_2-$ or a direct bond between the adjacent C atoms, by the condensation of cycloalkanones of the formula

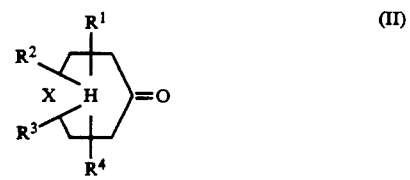

with anilines of the formula

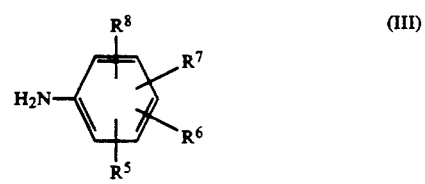

in which $R^1$ to $R^8$ and X have the above meaning, in the presence of acid heterogeneous catalysts with azeotropic removal of the water, which process is characterised in that the condensation reaction is carried out in a continuous reaction in a column-like reactor having an applied temperature profile, the starting materials being fed in in the low-temperature zone and, of the reaction products, the water of reaction to be removed as an azeotrope also being removed in the low-temperature zone and the azomethine formed being removed in the high-temperature zone.

DETAILED DESCRIPTION OF THE INVENTION

It is preferable to employ starting materials in which aryl is phenyl.

It is also preferred to employ cycloalkanones in which $R^4$ denotes hydrogen. It is also preferred to employ anilines in which $R^8$ denotes hydrogen.

It is particularly preferred to employ cycloalkanones in which $R^3$ and $R^4$ denote hydrogen.

It is also particularly preferred to employ anilines in which $R^7$ and $R^8$ denote hydrogen.

Furthermore, cycloalkanones of the formula

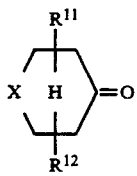

(IV)

in which $R^{11}$ and $R^{12}$ independently of one another denote hydrogen, linear or branched $C_1-C_4$-alkyl, cyclopropyl, cyclopentyl, cyclohexyl or phenyl and X denotes $-CH_2$ or a direct bond between the adjacent C atoms, are preferred.

It is particularly preferred to employ cycloalkanones of the formula

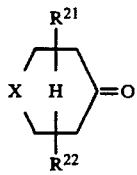

(V)

wherein $R^{21}$ and $R^{22}$ independently of one another denote hydrogen, methyl or ethyl and X has the above meaning.

It is also preferred to employ anilines of the formula

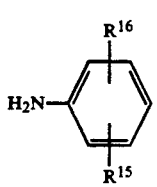

(VI)

in which $R^{15}$ and $R^{16}$ independently of one another denote hydrogen, linear or branched $C_1-C_4$-alkyl, phenyl, fluorine, chlorine, bromine, linear or branched $C_1-C_4$-alkoxy, hydroxyl, amino, $C_1-C_4$-alkylamino, di-$C_1-C_4$-alkylamino, phenoxy or phenylamino.

It is particularly preferable to employ anilines of the formula

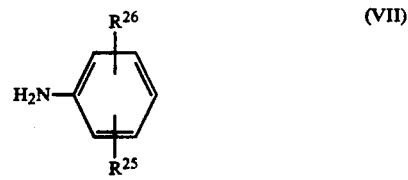

(VII)

in which $R^{25}$ and $R^{26}$ independently of one another denote hydrogen, methyl, ethyl, fluorine, chlorine, methoxy, ethoxy, methylamino, ethylamino, dimethylamino or diethylamino.

It is very particularly preferred to employ anilines of the formula

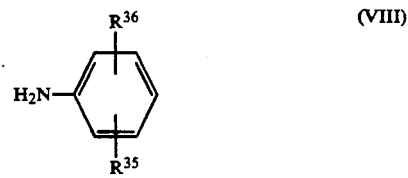

(VIII)

in which $R^{35}$ and $R^{36}$ independently of one another denote hydrogen, fluorine, chlorine, methyl, ethyl, methoxy, methylamino or dimethylamino.

Linear or branched $C_1-C_6$-alkyl groups, such as methyl, ethyl, propyl, isopropyl, butyl, isobutyl, tert.-butyl and the isomeric pentyls and hexyls, may be mentioned as alkyl groups in the substituents mentioned (alkyl, alkoxy, alkylamino or dialkylamino). Preferential mention may be made of the $C_1-C_4$-alkyl groups, particularly preferably methyl and ethyl and very particularly preferably methyl.

Phenyl or a 5-membered or 6-membered heteroaryl attached in the 2-, 3- or 4-position and having 1 or 2 hetero atoms belonging to the group N—O—S may be mentioned as aryl in the substituents mentioned (aryl, aryloxy or arylamino). The following are examples of heteroaryl of this type: furanyl, pyrrolyl, thienyl, pyrazolyl, imidazolyl, oxazolyl, thiazolyl, pyridyl and others. Aryl preferably is phenyl.

Cyclopropyl, cyclobutyl, cyclopentyl and cyclohexyl, preferably cyclopropyl, cyclopentyl and cyclohexyl, may be mentioned as examples of $C_3-C_6$-cycloalkyl. The cycloalkyl substituents can, in turn, be monosubstituted or disubstituted by methyl or ethyl.

Fluorine, chlorine, bromine and iodine, preferably fluorine, chlorine and bromine, and particularly preferably fluorine and chlorine, may be mentioned as examples of halogen.

The term "X" in the cycloalkyl ring in the formulae (I), (IV) and (V) can denote the methylene group $-CH_2-$ or a direct bond between the adjacent C atoms. The first case represents the cyclohexane skeleton, the second case represents the cyclopentane skeleton. X preferably denotes the methylene group and thus constitutes the cyclohexane skeleton.

The following cycloalkanones may be listed individually as examples of starting compounds: cyclopentanone, 2-methylcyclopentanone, 2-ethylcyclopentanone, 2-phenylcyclopentanone, cyclohexanone, 2-methylcyclohexanone, 4-methylcyclohexanone, 2-ethylcyclohexanone, 4-ethylcyclohexanone, 4-phenylcyclohexanone, 2-phenylcyclohexanone, 4-cyclohexylcyclohexanone and 2-cyclohexylcyclohexanone.

The following anilines may be listed individually as examples of starting compounds: aniline, 2-methylaniline, 3-methylaniline, 4-methylaniline, 2,4-dimethylaniline, 2-ethylaniline, 4-ethylaniline, 3-methoxyaniline, 3-ethoxyaniline, 4-aminoaniline, 4-methylaminoaniline, 4-dimethylaminoaniline, 4-phenylaniline, 2-phenylaniline, 4-phenoxyaniline, 2-phenoxyaniline, 4-phenylaminoaniline, 2-phenylaminoaniline, 2-fluoroaniline, 4-fluoroaniline, 2-chloroaniline and 4-chloroaniline.

The molar ratio in which the cycloalkanone and the aniline are charged is from 2:1 to 1:2, preferably from 1.5:1 to 1:1.5, particularly preferably from 1.2:1 to 1:1.2 and particularly preferably from 1.1:1 to 1:1.1.

Azeotrope-formers belonging to the group of aliphatic and aromatic hydrocarbons, aliphatic and aromatic ethers and aliphatic alcohols can be employed for the azeotropic removal of the water of reaction. Hydrogen atoms can be replaced by halogen atoms in these compounds. These azeotrope-formers, their mode of action and their use are known well to those skilled in the art. The following may be listed as examples of azeotrope-formers: benzene, toluene, xylene, anisole, chlorobenzene, butanol, hexanol, methyl butyl ether, diphenyl ether and p-chloroanisole. The ratio by weight in which an azeotrope-former and the total of the starting materials are charged is 0.001–1:1, preferably 0.001–0.5:1, particularly preferably 0.001–0.2:1 and very particularly preferably 0.001–0.1:1. The azeotrope removed by distillation can be condensed outside the column-like reactor and separated into water of reaction and azeotrope-former, in a manner known to those skilled in the art. The azeotrope-former thus recovered can again be recycled into the reaction of the process according to the invention.

One of the starting materials, preferably the cycloalkanone, can also be used as the azeotrope-former, so that it is possible to dispense with an azeotrope-former extraneous to the system.

Suitable acid heterogeneous catalysts are acid, inorganic or organic solids. Examples of acid, organic solids are acid ion exchangers, preferably having a macroporous structure, such as are known from German Auslegeschrift 1,113,570, German Offenlegungsschrift 1,595,700 and German Offenlegungsschrift 2,525,295. These are sulphonated polystyrene resins and polyacrylic acid resins. Perfluorinated organic sulphonated resins can also be used. It is also possible to employ acid phenol/formaldehyde or phenol/melamine resins.

Inorganic solids having an acid reaction which may be mentioned are oxides of metals of a medium and high stage of oxidation and mixed oxides thereof. As well as metal oxides, the oxides of certain non-metals or metalloids are also suitable. The following may be mentioned as example of metals, non-metals and metalloids of this type: $boron^{3+}$, $aluminium^{3+}$, rare $earths^{3+}$, $silicon^{4+}$, $germanium^{4+}$, $tin^{4+}$, $titanium^{4+}$, $zirconium^{4+}$, $hafnium^{4+}$, $vanadium^{3+}$, $vanadium^{5+}$, $niobium^{5+}$, $tantalum^{5+}$, $chromium^{3+}$, $chromium^{6+}$, $molybdenum^{6+}$, $tungsten^{6+}$ and $zinc^{2+}$. Particularly preferred amongst these are acid oxides and mixed oxides having a content of aluminium oxide, particularly preferably acid aluminium silicates, for example those having a layer structure (clays) and acid aluminosilicates of defined microporosity (zeolites).

The following are examples of acid inorganic oxidic solids: boehmite, $\gamma$-$Al_2O_3$, montmorillonite, bentonite, mica, H-ZSM 11, H-ZSM 5, H-mordenite, H-Y, SE-Y, H-$\Omega$, H-L, H-offretite, H-ZSM12, H-ZSM23 and H-ferrierite. For use in accordance with the invention, inorganic oxides and mixed oxides have a BET surface area of 40 to 400 $m^2/g$, preferably 50–350 $m^2/g$ and particularly preferably 100–300 $m^2/g$. Especially in the case of zeolites the range of BET surface area is 20–800 $m^2/g$, preferably 30–600 $m^2/g$ and particularly preferably 40–400 $m^2/g$. The pH of a suspension of such inorganic oxides or mixed oxides, composed of 1 g of finely ground oxide or mixed oxide in 40 ml of 1N aqueous NaCl solution should be between 0 and 7, preferably 1–6 and particularly preferably 2–5.

In principle, such organic or inorganic solids which can be employed as acid heterogeneous catalysts can have any desired shape. However, in order to maximise the loading capacity of the column-like reactor, care should be taken above all to have a gas stream which is not greatly impeded (pressure drop in the column as low as possible). This is achieved, inter alia, by selecting the shape and size of the particles in accordance with the shape and size of customary packings for distillation columns. For this purpose the inorganic or organic solids are shaped by means of suitable binders, such as are known to those skilled in the art, to give appropriately pelletised packings, extrudates, Raschig rings, Pall rings, saddle packings and others. The organic or inorganic solids can, however, also be applied and bound, in the form of a fine powder, to inert ceramic bodies of a suitable shape. The techniques for the production of such mouldings are known in principle to those skilled in the art. Amongst the organic and inorganic solids mentioned, the inorganic solids are preferred because of their higher heat resistance.

The weight hourly space velocity over the organic or inorganic solids mentioned as acid heterogeneous catalysts, expressed in g/g.hour, is 0.1–10, preferably 0.2–6, particularly preferably 0.3–5 and very particularly preferably 0.4–3.

The process according to the invention comprises carrying out the condensation reaction in a column-like reactor suitable for continuous reactions, and a temperature profile is applied to its longitudinal axis. With the exception of addition and removal zones for the reactants and products, the column-like reactor is packed, at least partially, with an acid heterogeneous catalyst in the pelletised form described above, somewhat in the manner of a distillation column. In the event that the column-like reactor is not packed completely with the acid heterogeneous catalyst, the sections not packed with catalyst contain inert packing such as is known for distillation purposes to those skilled in the art, shaped somewhat in the manner mentioned above, or these sections of the reactor not packed with catalyst contain column plates, somewhat in the shape of bubble cap plates. The sections of the column-like reactor which are packed with catalyst or with inert packing are of course terminated by sieve plates of a suitable mesh width in order to prevent the catalyst or packing from being washed away. The packing sections of the reactor can also contain bubble cap plates which, of course, are terminated by sieves in the described manner.

In principle, the column-like reactor can widen or narrow in various sections of its total length, particularly in the sections packed with catalyst. However, to simplify handling when charging the reactor with catalyst or packing, it is preferable to use as the reactor a tube without such changes in radius or at most with one wide section. Within the limits of the at least partial charging, the catalyst is located in any desired section of the column-like reactor, with due regard to the temperature profile described later in the text. A zone between the upper and lower eighth, preferably between the upper and lower quarter and particularly preferably between the upper and lower third of the total length of the column-like reactor may be mentioned as an optional section of this kind for charging with catalyst.

In accordance with the invention a temperature profile is applied to the column-like reactor. This temperature profile embraces the temperature range from 10° to 300° C., preferably 15° to 250° C. and particularly preferably 20° to 200° C. In order to set up the temperature gradient in the individual sections of the column-like reactor these sections are provided with insulation or with thermostatic control such as is customary in the construction of chemical apparatus. The thermostatic control in this case can be heating or cooling, as desired.

The sections of the column-like reactor which are packed with the acid heterogeneous catalyst should have a temperature not higher than 250° C., preferably not higher than 200° C. and particularly preferably not higher than 150° C.

The temperature range for such sections, packed with catalyst, is, accordingly, preferably 25°–160° C., particularly preferably 30°–150° C. and very particularly preferably 40°–140° C. The said adjustment of temperature for the sections of the reactor charged with catalyst can be maintained in a known manner by means of insulation or complete or partial thermostatic control, preferably by means of insulation.

The section of the reactor above the catalyst packing has a lower temperature than the catalyst packing, for example 15°–100° C., preferably 10°–80° C. and particularly preferably 5°–70° C. less than the catalyst packing. The section of the reactor below the catalyst packing has a higher temperature than that of the catalyst packing, for example 20°–100° C., preferably 25°–90° C. and particularly preferably 25°–80° C. higher than the catalyst packing. In this case the lower temperature above the catalyst packing can decrease towards the upper end of the reactor continuously or in several stages. The temperature of the reactor below the catalyst packing can correspondingly increase towards the lower end of the reactor continuously or over a plurality of sections. Depending on the desired setting of this decreasing or increasing temperature, the setting can be effected merely by insulation or by appropriate thermostatic control (cooling or heating). A temperature gradient can also be applied along the length of the catalyst packing, with lower temperatures towards the top and higher temperatures towards the base. In every case the column-like reactor is heated at its lower end, in particular via a heating coil, a heated jacket or external heating. The equipment of the column-like reactor also preferably includes a bottoms circulation for the azomethine to be removed as the process product. The temperature of the heating medium for heating the lower section of the column together with the bottoms circulation should not be higher than 100° C., preferably not higher than 80° C., particularly preferably not higher than 60° C. and very particularly preferably not higher than 40° C., than the boiling point of the azomethine to be removed as product under the particular pressure prevailing in the column.

Below the catalyst packing an additional thermostatic control is preferably fitted, so that the temperature between the catalyst packing and the end of the reactor can be set. The heat transfer fluid for this thermostatic control should have a reflux temperature of not higher than 60° C., preferably not higher than 40° C. and particularly preferably not higher than 20° C., above the boiling point of the contents of the column at this point, under the operating pressure prevailing there.

The process according to the invention is carried out within a pressure range from 0.5 mbar to 3 bar, preferably 1 mbar to 1 bar, particularly preferably 2–250 mbar and very particularly preferably 3–180 mbar. For the preferred operation in the sub-atmospheric pressure range the column-like reactor is equipped at its upper, low-temperature end with a vacuum pump, which can be installed upstream or downstream of the condenser for the water to be removed azeotropically.

The starting materials can be fed into the reactor individually or as a mixture above the catalyst at any desired point in the low-temperature zone. They are preferably fed in as a mixture immediately above the catalyst packing. In a particularly preferred embodiment the mixture is fed into the reactor at the point at which the proportions of the starting materials in the liquid phase in the reactor are the same as the proportions of the mixture to be fed in. In the event that, owing to its greater volatility, one of the starting materials is under-represented in the catalyst packing, it can, nevertheless, be fed in wholly or partly below the catalyst packing and can thus wholly or partly be passed countercurrent to the other reactant.

If a separate azeotrope-former is employed, it can also be fed in separately from the starting materials; however, it is preferable to feed it in with the mixture of the starting materials or at least mixed with one of the starting materials.

The azomethine is removed as the reaction product at the lower end of the reactor in the high-temperature zone, for example from the bottoms circulation. The product is normally very pure and can be used for other purposes without further purification. In the event that sparingly volatile by-products are to be removed, the desired azomethine can be removed from the column-like reactor in a manner known in principle to process engineers at a point above the take-off for such sparingly volatile by-products, in particular at a point where maximum purity is ensured.

In a preferred embodiment a stream of inert gas is fed in in the high-temperature zone, i.e. in any case below the catalyst packing, countercurrent to the azomethine removed in the high-temperature zone. The following may be mentioned as examples of inert gases: air, nitrogen, argon or methane, all of which are preferably employed in an anhydrous form.

The water of the reaction is removed as an azeotrope at the upper end of the column-like reactor, that is to say in the low-temperature zone, and is separated in a separating vessel into an aqueous phase and an organic phase of the azeotrope-former. The organic phase is preferably recycled to the reactor, particularly if one of the reactants is at the same time the azeotrope-former;

this can be effected at one of the points mentioned above.

Compared with the state of the art, the advantage of the process according to the invention is that it makes it possible to employ virtually equimolar amounts of the starting materials, which can then be reacted completely in a single pass. A quantitative yield is achieved in this way, with the avoidance of additional stages of working up. The reactor to be used is distinguished by great simplicity and by optimum utilisation of the energy employed. The azomethines which can be prepared in accordance with the invention are starting materials for hydrogenation to give cyclohexylcycloalkylamines and phenylcycloalkylamines and, in the event that the cycloalkanone is a cyclohexanone, for dehydrogenation to give optionally substituted diphenylamines.

EXAMPLES

Determination of acidity

The surface acidity is determined by suspending 1 g of catalyst granules, ground into powder, in 40 ml of 1N aqueous NaCl solution. The pH of the suspension was determined by means of a glass electrode measuring cell, and the amount of acid was titrated potentiometrically with 0.1N NaOH at a drop rate of 0.1 ml/minute. The values measured are shown in Table 1.

The granule samples were ground in a Mikro-Dismembrator (Braun, Melsungen AG). 5 ml of the granules and a tungsten carbide sphere having a diameter of 9 mm were put into the lower section of a grinding vestole. The vestole was put into the shaking container made of PTFE with the upper section closed. The shaking container was attached to the holder of the dismembrator and the amplitude of oscillation was adjusted to a deflection of approx. 10 mm. Grinding was complete after 6 to 8 minutes. The finely divided powder could then be employed for the above determination of acidity.

EXAMPLE 1

A mirror-coated vacuum column of length 80 cm and internal diameter 2.5 cm was packed to a height of 15 cm with glass Raschig rings, packed to 65 cm with 200 g of zeolite H-ZSM 11 granules of dimensions 2×6 mm, bound with 15% of $SiO_2$, and the packing was completed with 15 cm of Raschig rings. At its lower end the column was provided with a vaporiser tube 30 cm in length and of internal diameter 2.5 cm, which was packed with Raschig rings and could be thermostatically controlled. The column head consisted of a distillation bridge equipped with a thermometer and a metering dropping funnel. Both the vaporiser and the bridge were each provided with a vacuum take-off unit for the discharge of liquids. The lower unit was attached to a rotameter having a membrane metering valve. The distillation bridge was connected to a water pump having an electronically controlled ultimate vacuum, and the pressure was adjusted to 60 mbar. A countercurrent of nitrogen was adjusted to 14 l of $N_2$/minute at 60 mbar.

A mixture of cyclohexanone and aniline in a molar ratio of 1.2:1.0 dripped at a rate of 120 g/hour onto the top packing of Raschig rings. The vaporiser was thermostatically controlled at 180° C. Steady-state conditions became established after a short starting-up phase. Whereas 98.6 g/hour of 100% strength anil, contaminated with traces of less than 0.1% of higher-boiling components, issued at the vaporiser outlet, a mixture of 10.2 g/hour of water and 11.2 g/hour of cyclohexanone condensed at the column head at a temperature of 45° to 48° C. The apparatus was operated for 1000 hours without deactivation of the catalyst.

EXAMPLE 2

A 90 cm column having a thermostatically controllable zone 15 cm long and 30 cm distant from the lower end was provided with the peripheral equipment described in Example 1. The apparatus was packed with Raschig rings up to 45 cm, i.e. to the end of the liquid-filled jacket. A layer, 20 cm thick, composed of 45 g of KAO, a proton-exchanged montmorillonite made by Südchemie, having particle sizes of 3–4 mm, was then put in and the column was filled up with Raschig rings. 45 g per hour of a mixture of 1.2 mol of cyclohexanone and 1 mol of aniline were metered in at 60 mbar with a nitrogen countercurrent of 2 to 3 l/hour. The vaporiser temperature was set at 200° C. and the liquid-filled jacket was thermostatically controlled at 105° C. 37 g/hour of anil were produced at the vaporiser outlet, while the azeotrope, consisting of 3.9 g of water and 4.2 g of cyclohexanone condensed at the head of the column at a temperature of 45°–48° C. The apparatus was operated for 100 hours without loss of activity. The test was terminated without an indication of an incipient loss of activity.

EXAMPLE 3

A 135 cm column (internal diameter 2.5 cm), having a thermostatically controllable zone 20 cm long and 35 cm distant from the lower end and a thermostatically controllable zone 10 cm long and 95 cm distant from the lower end, was provided with the peripheral equipment described in Example 1. 110 g of KAO (2–3 mm) were put into the 40 cm long insulated zone between the thermostatically controllable zones, and the remainder of the column was given a packing of Raschig rings. 275 g per hour of a mixture of 1.18 mol of cyclohexanone and 1 mol of aniline were metered into the upper thermostatically controllable zone at 60 mbar, with a nitrogen counter-current of 0.1 to 0.2 l/hour. The vaporiser temperature was set at 210° C., the temperature of the lower thermostatically controlled zone at 115° C. and the temperature of the upper thermostatically controlled zone at 35° C. 228 g/hour of anil were produced at the vaporiser outlet, while the azeotrope, consisting of 23.7 g/hour of water and 23.3 g/hour of cyclohexanone condensed at the head of the column at 39°–40° C. The apparatus was operated for 800 hours without loss of activity and the test was terminated without indication of incipient deactivation. Table 1 below shows the results obtained with the catalyst KAO and results obtained with other catalysts.

TABLE 1

The catalysts employed in Example 3, the pH values measured and the conversions and selectivities achieved by means of them.

| Catalyst | Remarks | pH | Conversion % | Selectivity % |
|---|---|---|---|---|
| $Al_2O_3$ | Pural SCF (Condea) | 6.8 | 100 | 97 |
|  | SPH 512 (Rh.-Poulenc) | 9.1 | 20* | 100 |
|  | Disperal spez 10/1 (Condea) | 6.9 | 100 | 99 |
|  | $Al_2O_3$ active (Johnson Matthey) | 9.4 | 10* | 100 |

TABLE 1-continued

The catalysts employed in Example 3, the pH values measured and the conversions and selectivities achieved by means of them.

| Catalyst | Remarks | pH | Conversion % | Selectivity % |
|---|---|---|---|---|
| Sheet silicates | KA0 (Südchemie) | 4.1 | 100 | 100 |
| | KA1 (Südchemie) | 3.4 | 100 | 100 |
| | KA2 (Südchemie) | 4.2 | 100 | 100 |
| | KA3 (Südchemie) | 5.0 | 100 | 100 |
| | K306 (Südchemie) | 3.5 | 100 | 100 |
| | KP-10 (Südchemie) | 2.4 | 100 | 100 |
| | KS (Südchemie) | 2.8 | 100 | 99 |
| | KSF/o (Südchemie) | 1.9 | 100 | 100 |
| | KSF (Südchemie) | 2.3 | 100 | 100 |
| Zeolites (modules), all bound with 15% of $SiO_2$ | H-ZSM 11 (110) | 4.0 | 100 | 100 |
| | H-ZSM 11 (54) | 2.4 | 100 | 100 |
| | H-ZSM 5 (326) | 2.9 | 100 | 100 |
| | H-ZSM 5 (180) | 2.8 | 100 | 100 |
| | H-mordenite (12.5) | 2.9 | 100 | 100 |
| | H-Y (25.0) | 3.9 | 100 | 100 |
| | SE-Y (12.0) | 4.4 | 100 | 100 |

*The conditions indicated in Example 3 did not become established on the contrary the bulk of the mixture of starting materials metered in distilled off via the head of the column.

What is claimed is:

1. A process for the preparation of an azomethine of the formula

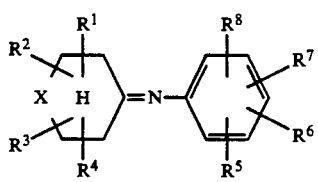

in which $R^1$, $R^2$, $R^3$, $R^4$, $R^5$, $R^6$, $R^7$ and $R^8$ independently of one another denote hydrogen, linear or branched $C_1$-$C_6$-alkyl, $C_3$-$C_6$-cycloalkyl, benzyl or aryl, and $R^5$, $R^6$, $R^7$ and $R^8$ independently of one another additionally denote halogen, linear or branched $C_1$-$C_6$-alkoxy, hydroxyl, amino, $C_1$-$C_6$-alkylamino, di-$C_1$-$C_6$-alkylamino, aryloxy or arylamino, aryl representing phenyl or 5-membered or 6-membered heteroaryl attached in the 2-, 3- or 4-position and having 1 or 2 hetero atoms belonging to the group N, O and S, and X denotes —$CH_4$— or a direct bond between the adjacent C atoms, comprising the condensation of a cycloalkanone of the formula

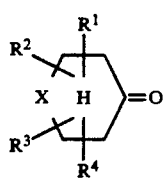

with an aniline of the formula

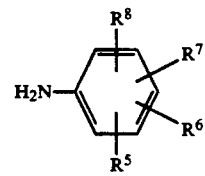

in which $R^1$ to $R^8$ and X have the above meaning, in the presence of an acid heterogeneous catalyst with azeotropic removal of the water of reaction, wherein the condensation reaction is carried out at a molar ratio of cycloalkanone to analine of 2:1-1:2, a pressure of 0.5 mbar-3 bar and in a continuous reaction in a column-like reactor having an applied temperature profile, ranging from 10° C. to 300° C. the starting materials being fed in in the low-temperature zone and, of the reaction products, the water of reaction to be removed as an azeotrope also being removed in the low-temperature zone and the azomethine formed being removed in the high-temperature zone.

2. The process of claim 1, wherein a cycloalkanone of the formula

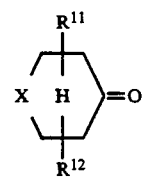

wherein $R^{11}$ and $R^{12}$ independently of one another denote hydrogen, linear or branched $C_1$-$C_4$-alkyl, cyclopropyl, cyclopentyl, cyclohexyl, benzyl or phenyl and X denotes —$CH_2$— or a direct bond between the adjacent C atoms, is employed.

3. The process of claim 2, wherein a cycloalkanone of the formula

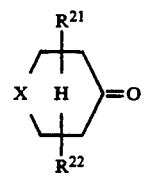

wherein $R^{21}$ and $R^{22}$ independently of one another denote hydrogen, methyl or ethyl and X denotes —$CH_2$— or a direct bond between the adjacent C atoms, is employed.

4. The process of claim 1, wherein the cycloalkanone is a cyclohexanone.

5. The process of claim 1, wherein an aniline of the formula

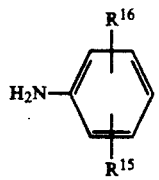

in which
R$^{15}$ and R$^{16}$ independently of one another denote hydrogen, linear or branched C$_1$–C$_4$-alkyl, phenyl, fluorine, chlorine, bromine, linear or branched C$_1$–C$_4$-alkoxy, hydroxyl, amino, C$_1$–C$_4$-alkylamino, di-C$_1$–C$_4$-alkylamino, phenoxy or phenylamino,
is employed.

6. The process of claim 5, wherein an aniline of the formula

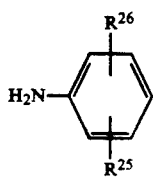

in which
R$^{25}$ and R$^{26}$ independently of one another denote hydrogen, methyl, ethyl, fluorine, chlorine, methoxy, ethoxy, methylamino, ethylamino, dimethylamino or diethylamino,
is employed.

7. The process of claim 6, wherein an aniline of the formula

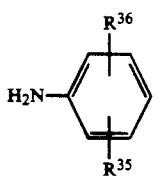

in which
R$^{35}$ and R$^{36}$ independently of one another denote hydrogen, fluorine, chlorine, methyl, ethyl, methoxy, methylamino or dimethylamino,
is employed.

8. The process of claim 1, wherein the cycloalkanone and the aniline are employed in a molar ratio of 1.5:1–1:1.5.

9. The process of claim 1, wherein the cycloalkanone and the aniline are employed in a molar ratio of 1.2:1–1:1.2.

10. The process of claim 1, wherein the cycloalkanone and the aniline are employed in a molar ratio of 1.1:1–1:1.1.

11. The process of claim 1, wherein said column-like reactor is a packed column, and, with the exception of addition and removal zones for the reactants and reaction products, is packed at least partially with an acid heterogeneous catalyst in a pelletised form.

12. The process of claim 11, wherein the sections of the column-like reactor which are not packed with catalyst are packed with inert packing in a pelletised form or are equipped with distillation plates.

13. The process of claim 12, wherein the distillation plates are bubble cap plates.

14. The process of claim 1, wherein the sections of the reactor packed with catalyst are at a temperature not higher than 250° C.

15. The process of claim 14, wherein the temperature profile applied is within the range from 15° to 250° C., the sections of the reactor packed with catalyst having a temperature not higher than 200° C.

16. The process of claim 15, wherein the temperature profile applied is within the range from 20° to 200° C., the sections of the reactor packed with catalyst having a temperature not higher than 150° C.

17. The process of claim 1, further comprising a stream of inert gas fed to the high-temperature zone countercurrent to the azomethine removed in the high-temperature zone.

18. The process of claim 1, wherein the reaction is carried out under a pressure of 1 mbar–1 bar.

19. The process of claim 1 wherein R$^3$, R$^4$, R$^7$, and R$^8$ each denotes hydrogen and X denotes —CH$_2$—.

* * * * *